(12) United States Patent
Cunningham, Jr.

(10) Patent No.: US 8,915,877 B2
(45) Date of Patent: Dec. 23, 2014

(54) GLAUCOMA DRAINAGE DEVICE AND USES THEREOF

(76) Inventor: Emmett T. Cunningham, Jr., Hillsborough, CA (US)

( * ) Notice: Subject to any disclaimer, the term of this patent is extended or adjusted under 35 U.S.C. 154(b) by 0 days.

(21) Appl. No.: 13/272,062

(22) Filed: Oct. 12, 2011

(65) Prior Publication Data

US 2012/0089073 A1   Apr. 12, 2012

Related U.S. Application Data

(60) Provisional application No. 61/392,309, filed on Oct. 12, 2010.

(51) Int. Cl.
*A61F 9/00* (2006.01)
*A61M 27/00* (2006.01)
*B82Y 5/00* (2011.01)
*A61F 9/007* (2006.01)

(52) U.S. Cl.
CPC .............. *A61F 9/00781* (2013.01); *B82Y 5/00* (2013.01)
USPC .................................. 604/9; 604/8

(58) Field of Classification Search
CPC ................................ A61F 9/00; A61M 27/00
USPC .......................................... 604/8, 9
See application file for complete search history.

(56) References Cited

U.S. PATENT DOCUMENTS

| 4,087,867 A | 5/1978 | Hickmann et al. |
| 4,089,329 A | 5/1978 | Couvillon, Jr. et al. |
| 4,554,918 A | 11/1985 | White |
| 4,863,457 A | 9/1989 | Lee |
| 4,922,913 A | 5/1990 | Waters, Jr. et al. |
| 4,936,825 A | 6/1990 | Ungerleider |
| 5,041,081 A | 8/1991 | Odrich |
| 5,127,901 A | 7/1992 | Odrich |
| 5,180,362 A | 1/1993 | Worst |
| 5,300,020 A | 4/1994 | L'Esperance, Jr. |
| 5,300,114 A | 4/1994 | Gwon et al. |
| 5,326,345 A * | 7/1994 | Price, Jr. ................ 604/9 |
| 5,370,607 A | 12/1994 | Memmen |
| 5,433,701 A | 7/1995 | Rubinstein |
| 6,142,969 A | 11/2000 | Nigam |
| 6,168,575 B1 | 1/2001 | Soltanpour |

(Continued)

FOREIGN PATENT DOCUMENTS

| WO | WO-99/01063 | 1/1999 |
| WO | WO-01/21063 | 9/2001 |
| WO | WO-2007/136993 | 11/2007 |

OTHER PUBLICATIONS

Kitco. "Gauge to Inches to Millimeters Conversion Table". <http://www.kitco.com/jewelry/gauge-inch-mm.html>. Oct. 12, 1999. See attached "Kitco Gauge Measurements" PDF.*

(Continued)

*Primary Examiner* — Susan Su
*Assistant Examiner* — Sara Sass
(74) *Attorney, Agent, or Firm* — Wilson Sonsini Goodrich & Rosati

(57) ABSTRACT

In one aspect, the present invention provides an implant device for use in an eye with elevated intraocular pressure or glaucoma. In another aspect, the present invention provides a method for lowering intraocular pressure and/or treating a condition associated with elevated intraocular pressure using the implant device of the present invention.

37 Claims, 2 Drawing Sheets

(56) References Cited

U.S. PATENT DOCUMENTS

| | | | |
|---|---|---|---|
| 6,443,893 | B1 | 9/2002 | Schnakenberg et al. |
| 6,468,283 | B1 | 10/2002 | Richter et al. |
| 6,579,235 | B1 | 6/2003 | Abita et al. |
| 6,638,976 | B2 | 10/2003 | Gamache et al. |
| 6,682,500 | B2 * | 1/2004 | Soltanpour et al. ............ 604/9 |
| 6,713,081 | B2 | 3/2004 | Robinson et al. |
| 6,730,056 | B1 * | 5/2004 | Ghaem et al. ................ 604/9 |
| 6,796,942 | B1 | 9/2004 | Kreiner et al. |
| 6,881,197 | B1 | 4/2005 | Nigam |
| 6,962,573 | B1 | 11/2005 | Wilcox |
| 7,247,702 | B2 | 7/2007 | Gardner et al. |
| 8,093,212 | B2 | 1/2012 | Gardner et al. |
| 8,206,333 | B2 | 6/2012 | Schmidt et al. |
| 8,308,701 | B2 | 11/2012 | Horvath et al. |
| 2003/0175324 | A1 | 9/2003 | Robinson et al. |
| 2003/0229303 | A1 | 12/2003 | Haffner |
| 2004/0170665 | A1 | 9/2004 | Donovan |
| 2004/0180075 | A1 | 9/2004 | Robinson et al. |
| 2004/0193095 | A1 | 9/2004 | Shadduck |
| 2004/0254517 | A1 | 12/2004 | Quiroz-Mercado et al. |
| 2005/0048099 | A1 | 3/2005 | Shiah et al. |
| 2005/0119601 | A9 | 6/2005 | Lynch et al. |
| 2005/0182350 | A1 | 8/2005 | Nigam |
| 2007/0190111 | A1 | 8/2007 | Robinson et al. |
| 2007/0248646 | A1 | 10/2007 | Hafezi-Moghadam et al. |
| 2007/0293807 | A1 | 12/2007 | Lynch et al. |
| 2008/0058704 | A1 * | 3/2008 | Hee et al. ................ 604/21 |
| 2008/0107712 | A1 | 5/2008 | Shiah et al. |
| 2008/0112923 | A1 | 5/2008 | Hughes et al. |
| 2008/0125691 | A1 * | 5/2008 | Yaron et al. ................ 604/9 |
| 2008/0131484 | A1 | 6/2008 | Robinson et al. |
| 2008/0145403 | A1 | 6/2008 | Spada et al. |
| 2008/0228127 | A1 | 9/2008 | Burns et al. |
| 2009/0214538 | A1 | 8/2009 | Fung et al. |
| 2009/0326432 | A1 | 12/2009 | Schmidt et al. |
| 2010/0100104 | A1 | 4/2010 | Yu et al. |
| 2010/0121249 | A1 | 5/2010 | Yu et al. |
| 2010/0234791 | A1 | 9/2010 | Lynch et al. |
| 2010/0272777 | A1 | 10/2010 | Robinson et al. |
| 2011/0071454 | A1 | 3/2011 | Dos Santos et al. |
| 2011/0071456 | A1 | 3/2011 | Rickard et al. |
| 2011/0071458 | A1 | 3/2011 | Rickard et al. |
| 2011/0071459 | A1 | 3/2011 | Rickard et al. |
| 2011/0251201 | A1 | 10/2011 | Huang et al. |
| 2011/0280829 | A1 | 11/2011 | David et al. |
| 2011/0309546 | A1 | 12/2011 | Shiah et al. |
| 2012/0089072 | A1 | 4/2012 | Cunningham |

OTHER PUBLICATIONS

Hong et al., "Glaucoma drainage devices: a Systematic Literature Review and Current Controversies," Survey of Ophthalmology, vol. 50, No. 1, January/February, pp. 48-60 2005.

Wolbarsht et al., "A scleral buckle pressure gauge for continuous monitoring of intraocular pressure," International Ophthalmology, vol. 3, No. 1, Dec. 1980.

U.S. Appl. No. 13/272,030 Office Action mailed May 5, 2014.

* cited by examiner

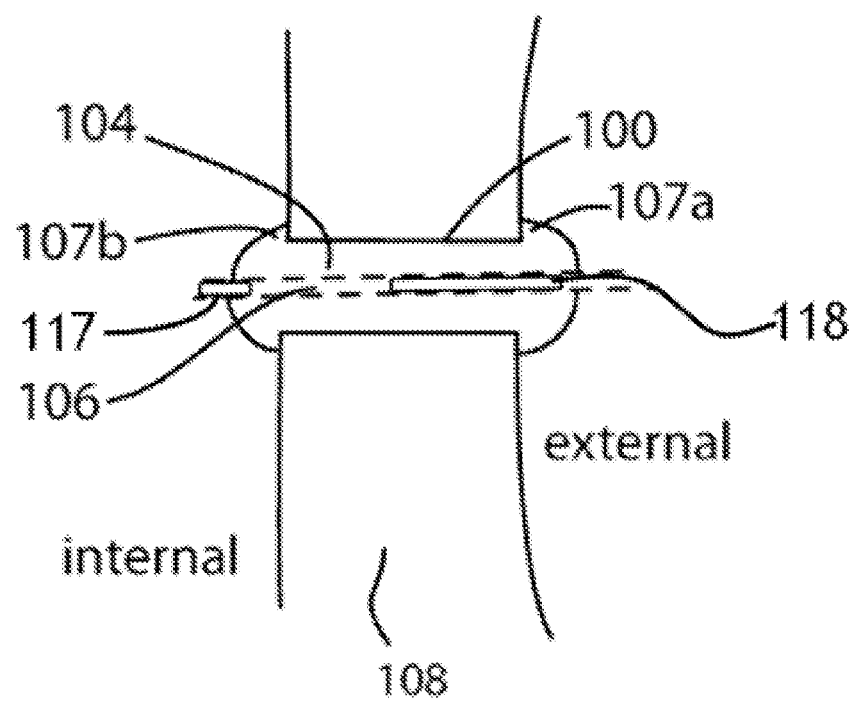

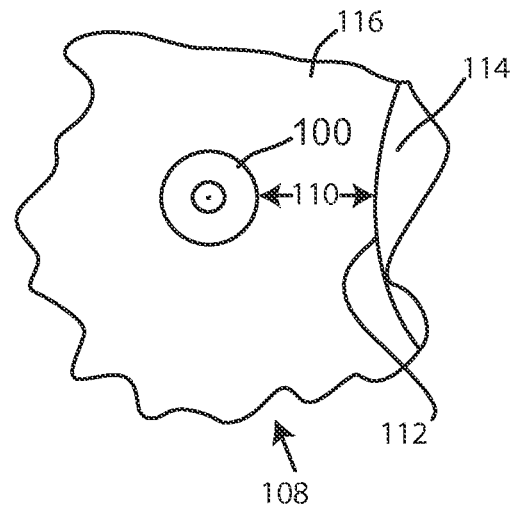
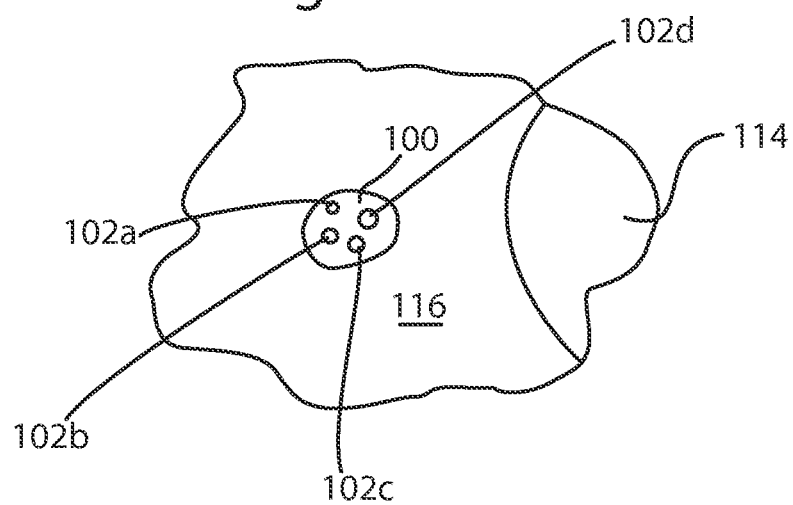

GLAUCOMA DRAINAGE DEVICE AND USES THEREOF

CROSS REFERENCE

This application claims priority to U.S. Provisional Application 61/392,309, filed Oct. 12, 2010, the contents of which are incorporated by reference in their entirety.

BACKGROUND OF THE INVENTION

Glaucoma is a major cause of blindness worldwide. The blindness that results from glaucoma can involve both central and peripheral vision and can have a major impact on an individual's ability to lead an independent and productive life. Pathophysiologically, glaucoma is an optic neuropathy (a disorder of the optic nerve) observed most typically in the setting of an elevated intraocular pressure. Dramatic and/or prolonged increases in intraocular pressure cause changes in the appearance ("cupping" or "excavation") and function ("scotomas" or "blind spots" in the visual field) of the optic nerve. If the pressure remains high enough for a long enough period of time, total, irreversible vision loss occurs. High intraocular pressure results from an imbalance in intraocular fluid production versus outflow. Glaucoma surgeries, also referred to as filtering procedures, are designed to improve intraocular fluid balance by augmenting fluid outflow, thereby lowering intraocular pressure.

Many techniques are available for treating an eye with an elevated intraocular pressure. These include various surgical techniques for facilitating flow of fluid from the inside of the eye to the subconjunctival space. The most commonly performed procedure, known as a trabeculectomy, involves creating a surgical fistula between the anterior chamber of the eye and the subconjunctival space. Less commonly, a surgical drainage device may facilitate flow of fluid between the anterior chamber and the subconjunctival space. Some such drainage devices, such as the Molteno, Ahmed, Kruppin, and Baerveldt valves, connect via a shunt tube to an externally fixated, subconjunctival reservoir. Modifications of these devices are available whereby the external reservoir and tube may facilitate flow from the posterior segment of the eye at the pars plana following removal of the vitreous to prevent clogging.

SUMMARY OF THE INVENTION

There is a need, therefore, for a device that allows direct drainage of intraocular fluid from the posterior chamber of the eye across the pars plana to the subconjunctival space in a controllable manner, without the need for a prior complete vitrectomy or an external reservoir.

In one aspect, the present invention is directed toward an implant for use in an eye with elevated intraocular pressure or glaucoma. The implant includes a tubular body portion having one or more lumens for diverting intraocular fluid from the vitreous cavity to the subconjunctival space at the pars plana; the tubular body portion terminating on one end at an inlet section and on another end at an outlet section, the tubular body portion being sized and shaped such that the inlet section is in close apposition to the intraocular surface at the pars plana and the outlet section rests on the sclera at the pars plana. The inlet section of the implant is configured for fluid communication with the outlet section via the one or more lumens. The inlet section is sized and shaped to fit in apposition to the intraocular surface at the pars plana so as to prevent dislocation or migration, and the outlet section is sized and shaped to fit in apposition to the surface of the sclera at the pars plana.

In some embodiments, the implant's tubular body portion has an 18 gauge or less external size.

In some embodiments, the implant's tubular body portion is configured for placement in isolation at the pars plana to provide for direct intraocular fluid flow from the vitreous cavity to the subconjunctival space.

In some embodiments, the implant's tubular body portion is configured for placement in connection with one or more devices in the subconjunctival space that are intended to enhance and/or direct intraocular fluid flow from the vitreous cavity to the subconjunctival space.

In some embodiments, the implant's one or more lumens are selectively controllable between an open and a closed position. The selectively controllable lumens can include a flow regulating member. The flow regulating member 118 can be a plurality of nanotubes, a plurality of capillary tubes, a plurality of collimated passages and combinations thereof. Alternatively, the flow regulating member can include a biological mechanoprotein used to regulate fluid flow. Alternatively, the flow regulating member 118 can be a membrane. Alternatively, the flow regulating member can be micromechanical valve.

In some embodiments, the implant's one or more lumens are reclosably openable.

In some embodiments, the one or more lumens can be initially closed and irreversibly openable. The irreversibly openable lumen can include a soluble barrier that is initially non-patent and over time due to the time-dependent erosion, dissolution or decomposition of the soluble barrier becomes patent. Or, the irreversibly openable lumen can include a barrier such as a membrane or plug that is initially non-patent and selectively opened using an external laser. Alternatively, the irreversibly openable lumen can include a barrier such as a membrane or plug that is initially non-patent and selectively opened using an external mechanical probe.

In some embodiments, each of the one or more lumens has a size that is different from the other of the one or more lumens. The size of each lumen can vary between 20 and 50 gauge.

In some embodiments, each of the one or more lumens is labeled so as to be differentiated from the other of the one or more lumens. The lumens can be labeled by having different colors.

In some embodiments, the inlet section of the lumen includes structures for minimizing clogging of the fluid communication at the inlet section by formed vitreous, blood, intraocular tissues, or scar formation. The structures can include a filter membrane, a surface corrugation, a surrounded cage structure, surface ridges, multiple ports, multiple perforations, and anti-clogging shaped structure. The anti-clogging shaped structure 117 can include spiral, a screw, or a helix-shaped structure, or combinations thereof.

In some embodiments, the outlet section of the implant includes a flange-like structure that is larger than the tubular body portion and the flange-like structure is sized and shaped to fit on the surface of the sclera at the pars plana so as to prevent the implant from dislocating or migrating.

In some embodiments, the inlet section of the implant includes a flange-like structure that is larger than the tubular body portion and the flange-like structure is sized and shaped to fit on the intraocular surface at the pars plana so as to prevent the implant from dislocating or migrating.

In some embodiments, at least a portion of the external surface of the tubular body portion includes securing structure for securing the implant in place near the pars plana. The securing structure can be a tissue adhesive, one or more barbs, a threading mechanism, a structure for suture placement, and combinations thereof.

In some embodiments, the device of the present invention is well fixated, that does not incite an immune or foreign body reaction that incites minimal inflammation, that has no sharp edges, and that can be easily placed into and removed from the eye.

The device 100 can be made of a material that is compatible with the tissues and fluids with which it is in contact. The device can be constructed of any number of bioerodible or non-bioerodible materials. In some embodiments, the implant is made of a biocompatible material including, but not limited to, titanium, stainless steel, silicone, polyurethane, ploylactic acid, polyvinyl alcohol, polyvinyl pyrolidone, collagen, heparinized collagen, polytetrafltioroethylene, expanded polytetrafluoroethylene, fluorinated polymer, fluorinated elastomer, flexible fused silica, polyolefin, polyester, polysilicon, polyorthoester, polyvinyl acid polymer, polyanhydride, polyglycolic, polyamide, parylene, composite of carbohydrates, polysaccharides and combinations thereof.

In some embodiments, the device is not absorbed, corroded, or otherwise structurally compromised during its in situ use. Moreover, the eye tissues and the aqueous remain non-detrimentally affected by the presence of the device 100. Examples of non-bioerodible materials include, but are not limited to, titanium, stainless steel, cobalt-chromium-nickle-molybdenum-iron alloy, nickel-titanium alloy, tantalum, metal, silicone, silicone polymer, polyurethane, plastic, acrylic polymer, or any combination thereof. In some embodiments, the device can be made of a biodegradable material selected from the group consisting of poly(lactic acid), polyethylene-vinyl acetate, poly(lactic-co-glycolic acid), poly(D,L-lactide), poly(D,L-lactide-co-trimethylene carbonate), poly(caprolactone), and poly(glycolic acid). In some embodiments, the device 100 is constructed of multiple polymeric layers of any bioerodible and/or non-bioerodible materials. In some embodiments, the material of the device 100 is smooth, textured, or corrugated. The device can be constructed as either porous or solid.

In some embodiments, the implant has one or more drug-eluting coatings. The drug-eluting coating can include an anti-inflammatory agent. The anti-inflammatory agent can include corticosteroids, immunosuppressive agents, non-steroidal anti-inflammatory drugs, anti-inflammatory proteins, peptides, or nucleic acids, and combinations thereof.

The drug-eluting coating can include a pressure lowering agent. The intraocular pressure lowing agent can be selected from the group consisting of an adrenergic agonist, cholinergic agonist, beta-blocker, carbonic anhydrase inhibitor, prostaglandin analogue, and alpha-adrenergic agonist.

In some embodiments, the drug-eluting coating can include an anti-proliferative agent. The anti-proliferative can include a corticosteroid, an immunosuppressive agent, mitomycin, 5-fluorouracil, heparin, anti-proliferative proteins, peptides, or nucleic acids and combinations thereof.

In some embodiments, the drug-eluting coating can include an anti-microbial agent, an intraocular pressure lowering agent, or a vitreolytic agent. The vitreolytic agent can include a dispase, urea, collagenase, hyaluronidase, plasmin, microplasmin, chondroitinase, a protease, and combinations thereof.

In some embodiments, the present invention is directed toward a method of lowering intraocular pressure. The method includes placing a self-contained transmural shunt device across the pars plana, where the device can provide for fluid communication between the vitreous cavity and the subconjunctival space, and where the device can reside entirely within the pars plana; and diverting intraocular fluid from the vitreous cavity to the subconjunctival space at the pars plana using the self-contained transmural shunt.

The implant devices in accordance with the embodiments of the present invention offer many advantages over known devices. Published United States Patent Application No. 2005/0119601 describes some of the known problems with existing shunt devices and highlights scarring and hypotony (low post-op pressure due to over filtration of the filter) as major problems with trabeculectomy surgery. These problems are also problems with shunts of all types. The implant device in accordance with the embodiments of the present invention addresses these known problems by incorporating drug eluting technology, so that an anti-scarring agent could be applied to the shunt; and by using multiple ports of different sizes that could be opened selectively and/or sequentially using fine probes that could even penetrate the intact conjunctiva post-operatively. In this way the IOP can be titrated. In addition to the '601 publication, most known shunt devices treat the eye by diverting fluid from the anterior chamber to the subconjunctival space. However, the implant device in accordance with the embodiments of the present invention is very different from the known implants in that it delivers fluid from the vitreous cavity or posterior chamber, through the pars plana, directly to the subconjunctival space without the use of a connecting tube or external reservoir. It is further differentiated in that prior removal of the vitreous is not required.

One advantageous feature is directed toward the placement of the device at the pars plana. The placement of the device at the pars plana reduces the potential for damage to, and occlusion by, anterior chamber structures.

Furthermore, the use of one or more lumens and the one or more flow regulating mechanisms enables the intraocular pressure to be controlled following the procedure. In addition, the problems such as double vision and limited eye movement that are typically encountered with shunting devices having external reservoirs are reduced if not eliminated.

Another advantage of the present implant device is that the use of a drug-eluting coating reduces the risk of occlusion by fibrosis and/or infection.

In another aspect, the present invention provides a method of lowering intraocular pressure and/or treating a condition associated with elevated intraocular pressure, the method comprising placing a self-contained transmural shunt device near the pars plana, the device providing fluid communication between the vitreous cavity and the subconjunctival space across the pars plana, the device residing entirely within the pars plana; and diverting intraocular fluid from the vitreous cavity to the subconjunctival space at the pars plana using the self-contained transmural shunt. In some embodiments, the method of the present invention further comprises an eye surgery, such as trabeculectomy.

For a further understanding of the nature and advantages of the invention, reference should be made to the following description taken in conjunction with the accompanying drawings.

BRIEF DESCRIPTION OF THE DRAWINGS

FIG. 1 shows a portion of the eye and the location across the pars plana where the implant device in accordance with the embodiments of the present invention is implanted.

FIG. 2 shows another view of the eye and the location across the pars plana where the implant device in accordance with the embodiments of the present invention is implanted.

DETAILED DESCRIPTION OF THE INVENTION

In one aspect, the present invention is directed to a glaucoma drainage device. In one embodiment, the device includes a tubular body portion having one or more lumens for diverting intraocular fluid from the vitreous cavity to the subconjunctival space across the pars plana. The location at the pars plana allows for the drainage of fluid from the eye without allowing the drainage device to touch the anterior chamber structures (e.g., iris and the cornea) or lens, as it is known that this touch can be major cause of complications and shunt failures. The tubular body portion ends on one end at an inlet section and on another end at an outlet section. The tubular body portion is sized and shaped such that the inlet section is in close apposition to the intraocular surface at the pars plana and the outlet section rests on the sclera at the pars plana. The inlet section can be configured for fluid communication with the outlet section via the one or more lumens. The inlet section is sized and shaped to fit in apposition to the intraocular surface in the vitreous body at the pars plana. The outlet section is sized and shaped to fit in apposition to the surface of the sclera at the pars plana so as to prevent dislocation or migration.

Device

FIG. 1 shows a portion of the eye 1, and the location near the pars plana where the implant device 100 in accordance with the embodiments of the present invention is implanted. FIG. 1A shows a device 100 across the eye wall and having a tube 104 having a central lumen 106 with an anti-clogging shaped structure 117, flow regulating member 118 and retaining flanges 107A and 107b. As is shown in FIG. 1B, the implant when in place is approximately 3.5-4 mm posterior to the corneal limbus 112 (shown as distance 110 in FIG. 1B) of the cornea 114 in the sclera 116. FIG. 1B shows a sectional view showing one embodiment of the device 100 as implanted in the eye across the pars plana 108.

The device shown in FIG. 1A is depicted as a single patent lumen device 100, however, it should be noted that there is no intention in limiting the device to a single patent lumen. FIG. 2 shows another view of the eye and the location across the pars plana near the cornea 114 in the sclera 116 where the implant device in accordance with the embodiments of the present invention is implanted. FIG. 2 shows the device 100 can include multiple lumens 102A-D where each lumen can have a different size. In some embodiments the device 100 includes a plurality of lumens. The lumens may be the same or different sizes, or a combination thereof. For non-limiting example, one lumen can be a 26 gauge lumen, a 27 gauge lumen, a 30 gauge lumen, a 35 gauge lumen. The lumens can be as small or smaller than an 18 gauge or as large as a 50 gauge lumen. In one embodiment, the lumens can be color coded to allow or facilitate the insertion of canalization probes of appropriate gauges.

In some embodiments, the device 100 can include a tube 104 having a central lumen 106 and retaining flanges 107A and 107B on both ends. The device once inserted through the eye wall at the pars plana allows for the redirection of intraocular fluid to the subconjunctival space. The implant 100 can be made of any number of biocompatible materials including, but not limited to titanium, stainless steel, silicone, polyurethane, polylactic acid, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, polyamide, parylene, and combinations thereof. More generally, the implant can be made of material selected from the group consisting of titanium, stainless steel, silicone, polyurethane, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and combinations thereof.

In some embodiments, the implant can be made of a biodegradable material. The biodegradable material may be selected from the group consisting of poly(lactic acid), poly-ethylene-vinyl acetate, poly(lactic-co-glycolic acid), poly(D,L-lactide), poly(D,L-lactide-co-trimethylene carbonate), poly(caprolactone), and poly(glycolic acid). The biodegradable material may comprise any biodegradable polymer, or any combination of biodegradable polymers.

The length of the tube portion 104 is chosen such that the inlet section (e.g., flanges and other inlet/outlet sections described below) would rest tightly against the inside of the eye near the pars plana, while the outlet section (e.g., flanges and other inlet/outlet sections described below) would rest against the external eye wall or sclera. One way of achieving this placement is to the have the implant be centered approximately 3.5 to 4.0 mm posterior of the corneoscleral junction (i.e. the limbus). Those skilled in the art will appreciate that that device placement can be performed alone or in conjunction with either the partial or complete surgical removal of the vitreous (i.e. vitrectomy). The removal of the vitreous can help minimize the risk of device clogging or failure. Other techniques for reducing or minimize the risk of device clogging or failure are also described below.

The overall outer dimension of the implant device can be dimensioned to facilitate its quick insertion following a 25 gauge, 23 gauge, or 20 gauge vitrectomy.

In one embodiment, the implant device has a drug eluting coating that allows for the addition of one or more agents to minimize post-surgical scarring or fibrosis, such as an anti-inflammatory agent (corticosteroids, immunosuppressive agents, NSAIDS, and so on) or an anti-proliferative agent (e.g., mitomycin, 5-fluorouracil, heparin and the like). Furthermore, the agent that is to be eluted can also have antimicrobial activity so as to help minimize the risk of infection following the procedure. In certain embodiments, the drug is incorporated into the device. In such an embodiment, the drug is not simply a coating, although it may also or alternatively be part of a coating on the device. The device itself, for non-limiting example, may have drug: within the device, within pores of the device, within a vessicle (or vessicles of) in the device, mixed with the polymer of the device, or some combination thereof. The drug may elute from the device itself, for example, as the device degrades (at a slower rate or faster rate or the same rate as the degradation rate of the device), or may elute from some portion of the device, such as through pores or microcracks in the device which do not affect the biostability or the placement or the effectiveness of the device itself (for example where the device comprises a non-degrading or durable polymer).

As disclosed hereinabove, the lumen 106 can be single patent lumen of appropriate size (e.g., approximately between 20 and 50 gauge) to permit the normalization of the intraocular pressure. The external opening of the lumen can be highlighted, for example by coloring, in such a way to make its location more pronounced. Alternatively, one or more lumens can be used for diverting intraocular fluid from the vitreous cavity to the subconjunctival space at the pars plana. The multiple patent lumens could be all of the same size or of variable sizes (e.g., between 20 and 50 gauge) to permit normalization of the intraocular pressure. Distinguishing highlights or colors can be sued to distinguish the external openings of various sized lumens.

The lumens can be configured whereby all, one or more of which are initially not patent, but which can be selectively opened to permit normalization of the intraocular pressure. Such opening or canalization of the lumens can be accomplished by using an instrument of appropriate gauge that fits into the lumen and thereby opens or dislodges what would otherwise permanently occlude the lumen.

The one or more lumens can contain a mechanism whereby insertion of a dilating or canalizing instrument could irreversibly dilate or open the lumen to the size of the instrument, such that insertion of instruments of progressively larger gauge would progressively and irreversibly dilate or open the one or more lumens. One such mechanism includes an adjustable diaphragm. Such an adjustable diaphragm can be controlled mechanically, or could use an electrical, magnetic and/or heat sensitive activation mechanism.

In some embodiments, the one or more lumens include one or more flow regulating mechanisms. Such flow regulating mechanisms can include carbon-based, silicon-based, or other polymer-based materials forming nanotubes, capillary tubes, collimated holes, and combinations thereof.

In some embodiments, the one more lumens include biological mechanoproteins, including, but not limited to, forisomes, that could be used to regulate fluid flow.

In some embodiments, the one or more lumens and/or the fluid regulating components are initially non-patent, and become patent over time due to the intentional time-dependant erosion, dissolution, or decomposition of a bioerodable or soluble barrier.

In some embodiments, the inlet section or the internal intraocular surface of the device has multiple openings or surface corrugations to reduce the risk of occlusion by the vitreous.

In some embodiments, the implant device in accordance with the embodiments of the present invention is a part of a kit that includes the canalization probes of varying sizes that can be used to open or reopen the lumens as is needed to establish and/or maintain intraocular pressure. In such case, the probes can have tapered tips to facilitate passage through the overlying conjunctiva and insertion into the lumen.

In some embodiments, the implant has one or more drug-eluting coatings. The drug-eluting coating includes but is not limited to an anti-inflammatory agent. The anti-inflammatory agent includes but is not limited to corticosteroids, immunosuppressive agents, non-steroidal anti-inflammatory drugs, anti-inflammatory proteins, peptides, or nucleic acids, and combinations thereof.

In some embodiments, the drug-eluting coating includes an anti-proliferative agent. The anti-proliferative agent includes but is not limited to a corticosteroid, an immunosuppressive agent, mitomycin, 5-fluorouracil, heparin, anti-proliferative proteins, peptides, or nucleic acids and combinations thereof.

In some embodiments, the drug-eluting coating includes but is not limited to an anti-microbial agent, an intraocular pressure lowering agent, or a vitreolytic agent. The anti-microbial agent can be selected from the group consisting of antiseptics, antibiotics, antivirals, antifungals, and antiparasites. The vitreolytic agent includes but is not limited to a dispase, urea, collagenase, hyaluronidase, plasmin, microplasmin, chondroitinase, a protease, and combinations thereof. The intraocular pressure lowing agent can be selected from the group consisting of an adrenergic agonist, cholinergic agonist, beta-blocker, carbonic anhydrase inhibitor, prostaglandin analogue, and alpha-adrenergic agonist.

Examples of other agents that can be eluted from the device of the present invention include but are not limited to anthracycline, doxorubicin, mitoxanthrone, fluoropyrimidine, 5-fluorouracil, a folic acid antagonist, methotrexate, podophylotoxin, etoposide, camptothecin, hydroxyurea, a platinum complex, cisplatin, anti-thrombotic agent, visualization agent, or echogenic material. In some embodiments, where growth is desired for stability, certain growth factors can be present, whereas at places where obstructions are to be avoided, certain antifibrotic agents can be present, such as 5-fluourouracil or mitomycin. In some embodiments, the device is more generally provided with coatings that are antibiotic, anti-inflammatory, or carboxylic anhydrase inhibitors. Agents that facilitate the degradation of collagen within the trabecular meshwork can also be employed.

In some embodiments, the drug eluting coating can include at least one therapeutic agent selected from the group consisting of a gene, a growth factor, and an enzyme.

In some embodiments, the device is used for a direct release of pharmaceutical preparations into ocular tissues. In some embodiments, the pharmaceuticals are compounded within the device, form a coating on the device. The device when coated or loaded with a slow-release substance can have prolonged effects on local tissue surrounding the device. The slow-release delivery can be designed such that an effective amount of substance is released over a desired duration. "Substance" or "therapeutic substance", as used herein, is defined as any therapeutic or active drug that can stop, mitigate, slow-down or reverse undesired disease processes. In some embodiments, a known drug therapy for treating glaucoma is utilized in combination with the present invention. A listing of some known drug therapies for treating glaucoma are discloses in U.S. Published Patent Application No. 20030229303, which is herein incorporated by reference in its entirety.

In some embodiments, the device is adapted for delivering the drug or agent locally to tissue proximate to the device. In some embodiments, the drug is released in the vicinity of the device 100 after deployment of the device. In some embodiments, the drug is released in effective concentrations from the device over a period ranging from the time of deployment of the device to about 1 year. In some embodiments, the drug is released in effective concentrations from the device at a constant rate, an increasing rate or a decreasing rate. In some embodiments, the device comprises more than one coating wherein the drugs eluted from the first coating and the second coating are the same or different. The coating can partially or completely cover the device 100. The coating can be uniform, non-uniform, discontinuous, or patterned.

Where the pharmaceutical delivery system of the present invention comprises a drug eluting polymer matrix, the drug eluting polymer can be conveniently made from siloxane copolymer, such as a fluorinated side-chain polysiloxane optionally polymerized with a comonomer such as methyl methacrylate, N,N-dimethylacrylamide, acrylamide, N-methylacrylamide, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, N-vinylpyrrolidione and hydroxybutyl methacrylate. By varying the concentration of the hydrophobic siloxane backbone, the polar —CF2H tail and any comonomer(s), if used, the hydrophobic/hydrophilic balance and hence the pharmaceutical agent release characteristics of the polymer coating can be controlled.

In some embodiments, the inlet section of the lumen includes structures for minimizing clogging of the fluid communication at the inlet section by formed vitreous, blood, intraocular tissues, or scar formation. The structures can include a filter membrane, a surface corrugation, a surrounded cage structure, surface ridges, multiple ports, multiple perforations, and anti-clogging shaped structure. The anti-clogging shaped structure 117 can include spiral, a screw, or a helix-shaped structure, or combinations thereof.

In some embodiments, the device comprises an outlet section of the implant that includes a flange-like structure that is larger than the tubular body portion and the flange-like structure is sized and shaped to fit on the surface of the sclera at the pars plana so as to prevent the implant from dislocating or migrating.

In some embodiments, the device comprises an external surface of the tubular body having a securing structure for securing the implant in place near the pars plana. In some embodiments, the securing structure is a tissue adhesive, one or more barbs, a threading mechanism, a structure for suture placement, or a combination thereof. In some embodiments, at least a portion of the external surface of the tubular body portion can include a securing structure for securing the implant in place near the pars plana. In some embodiments, the securing structure is a tissue adhesive, one or more barbs, a threading mechanism, a structure for suture placement, or a combination thereof.

In some embodiments, the device of the present invention can be used in connection with eye surgery, for example, trabeculectomy or vitrectomy.

In some embodiments, the device of the present invention can be either constructed with or used together with devices that are intended to monitor intraocular pressure over an extended period of time. For example, a noninvasive, continuous monitoring device for measuring intraocular pressure without interference with vision or normal activity of the patient is disclosed in U.S. Pat. No. 4,089,329, incorporated herein by reference in its entirety. A miniature, planar-faced pressure transducer is fixed in a protruding section of a compliant hydrogel ring that has been tooled to conform to the spherical surface of the sclera. The hydrogel ring is placed noninvasively under the eyelids within the conjunctival cul-de-sac, the transducer being located in the lower temperal quadrant. Applanation of the sclera against the planar surface of the transducer results as a consequence of pressure from the separated tissues. Intraocular pressure readings are based on the variations in resistance in the strain gage elements of the transducer caused by the applied stress to the transducer diaphragm. Other examples of intraocular pressure sensor or monitoring devices that can be used in conjunction with the device of the present invention include devices disclosed in U.S. Pat. No. 4,922,913, incorporated herein by reference in its entirety, and U.S. Pat. No. 6,579,235 incorporated herein by reference in its entirety, and International Application No. PCT/US2007/068536 incorporated herein by reference in its entirety, and in Myron L. Wolbarsht et al. International Ophthalmology Volume 3, Number 1/December 1980 herein incorporated by reference in its entirety. Exemplary devices for measuring intraocular pressure that can be used in conjunction with the device of the present invention include devices disclosed in U.S. Pat. Nos. 6,443,893 and 6,796,942, and EP Application Nos. 1213991B1 and 0981293B1, each of which are herein incorporated by reference in their entirety.

The implant device 100 in accordance with the embodiments of the present invention offer many advantages over known devices. One of the known problems with existing shunt devices and trabeculectomy is scarring and hypotony (low post-op pressure due to over filtration of the filter). The implant device in accordance with the embodiments of the present invention addresses these known problems by incorporating drug eluting technology, either intrinsically or through the use of a coating material. Anti-inflammatory, anti-microbial, and/or anti-scarring agent can be applied to the eye via the implant device. The use of a drug-eluting coating reduces the risk of occlusion by fibrosis and/or infection. One advantageous feature of the present invention is directed toward the placement of the device at the pars plana. The placement of the device at the pars plana reduces the potential for damage to, and occlusion by, anterior chamber structures.

Methods of Use

In another aspect, the present invention provides a method for lowering intraocular pressure, the method comprising placing the device of the present invention, the device providing for fluid communication between the vitreous cavity and the subconjunctival space across the pars plana, and diverting intraocular fluid from the vitreous cavity to the subconjunctival space across the pars plana using the self-contained transmural shunt. In some embodiments, the device resides entirely within the pars plana. In some embodiments, the intraocular fluid is drained to the subconjunctival space at a sufficient flow rate to reduce intraocular pressure. In some embodiments, the flow rate of the aqueous humor is below about 2.5 microliters per minute. In some embodiments, the flow rate of the aqueous humor is sufficient to maintain eye pressure above 6.0 mmHg. In some embodiments, the aqueous humor is produced by the eye at a rate that is about the same as the flow rate of aqueous humor through the device 100. In some embodiments, the flow rate in the presence of the device of the present invention maintains eye pressure between approximately 10 mmHg and 21 mmHg. In some embodiments, the intraocular fluid is drained at a sufficient flow rate to reduce build-up of the fluid in the anterior or posterior chamber or the vitreous cavity without hypotony.

In some embodiments, the device is used for treating an eye condition with high intraocular pressure. For example, the device can be used for treating glaucoma. Glaucoma can be divided roughly into two main categories, "open angle" or chronic glaucoma and "closed angle" or acute glaucoma. The device of the present invention can be used to treat both forms of glaucoma. The device can be used in conjunction with any existing surgery for treating glaucoma, for example, either topical medications or trabeculectomy.

Examples of the drug or agent that can be used in the present invention to reduce inflammation, scarring, fibrosis, infection, or enhance the therapeutic function or enhance healing include but are not limited to brefeldin A, a histamine receptor antagonist, an alpha adrenergic receptor antagonist, an anti-psychotic compound, a CaM kinase II inhibitor, a G protein agonist, an antibiotic selected from the group consisting of apigenin, ampicillin sodium salt, puromycin, an anti-microbial agent, a DNA topoisomerase inhibitor, a thromboxane A2 receptor inhibitor, a D2 dopamine receptor antagonist, a Peptidyl-Prolyl Cis/Trans Isomerase Inhibitor, a dopamine antagonist, an anesthetic compound, a clotting factor, a lysyl hydrolase inhibitor, a muscarinic receptor inhibitor, a superoxide anion generator, a steroid, an anti-proliferative agent, a diuretic, an anti-coagulant, a cyclic GMP agonist, an adenylate cyclase agonist, an antioxidant, a nitric oxide synthase inhibitor, an antineoplastic agent, a DNA synthesis inhibitor, a DNA alkylating agent, a DNA methylation inhibitor, a NSAID agent, a peptidylglycine alpha-hydroxylating monooxygenase inhibitor, an MEK1/MEK2 inhibitor, a NO synthase inhibitor, a retinoic acid receptor antagonist, an ACE inhibitor, a glycosylation inhibitor, an intracellular calcium influx inhibitor, an anti-emetic agent, an acetylcholinesterase inhibitor, an ALK-5 receptor antagonist, a RAR/RXT antagonist, an elF-2a inhibitor, an S-adenosyl-L-homocysteine hydrolase inhibitor, an estrogen agonist, a serotonin receptor inhibitor, an antithrombotic agent, a tryptase inhibitor, a pesticide, a bone mineralization promoter, a bisphosphonate compound selected from risedronate and an analogue or derivative thereof, an anti-inflammatory compound, a DNA methylation promoter, an anti-spasmodic agent, a protein synthesis inhibitor, an α-glucosidase inhibitor, a calcium channel blocker, a pyruvate dehydrogenase activator, a prostaglandin inhibitor, a sodium channel inhibitor, a serine protease inhibitor, an intracellular calcium flux inhibitor, a JAK2 inhibitor, an androgen inhibitor, an aromatase inhibitor, an anti-viral agent, a 5-HT inhibitor, an FXR antagonist, an actin polymerization and stabilization promoter, an AX0R12 agonist, an angiotensin II receptor agonist, a platelet aggregation inhibitor, a CB1/CB2 receptor agonist, a norepinephrine reuptake inhibitor, a selective serotonin reuptake inhibitor, a reducing agent, and a immuno-modulator selected from Bay 11-7085, (−)–arctigenin, idazoxan hydrochloride, an angiogenesis inhibitor, an apoptosis antagonist, an apoptosis activator, a beta 1 integrin antagonist, a beta tubulin inhibitor, a blocker of enzyme production in Hepatitis C, a Bruton's tyrosine kinase inhibitor, a calcineurin inhibitor, a caspase 3 inhibitor, a CC chemokine receptor antagonist, a cell cycle inhibitor, a cathepsin B inhibitor, a cathepsin K inhibitor, a cathepsin L inhibitor, a CD40 antagonist, a chemokine receptor antagonist, a chymase inhibitor, a collagenase antagonist, a CXCR antagonist, a cyclin dependent kinase inhibitor, a cyclooxygenase 1 inhibitor, a DHFR inhibitor, a cual integrin inhibitor, an elastase inhibitor, an elongation factor-1 alpha inhibitor, an endothelial growth factor antagonist, an endothelial growth factor receptor kinase inhibitor, an endotoxin antagonist, an epothilone and tubulin binder, an estrogen receptor antagonist, an FGF inhibitor, a farnexyi transferase inhibitor, a farnesyltransferase inhibitor, an FLT-3 kinase inhibitor, an FGF receptor kinase inhibitor, a fibrinogen antagonist, a histone deacetylase inhibitor, an HMGCoA reductase inhibitor, an ICAM inhibitor, an IL, ICE, and IRAK antagonist, an IL-2 inhibitor, an immunosuppressant, an inosine monophosphate inhibitor, an integrin antagonist, an interleukin antagonist, an inhibitor of type III receptor tyrosine kinase, an irreversible inhibitor of enzyme methionine aminopeptidase type 2, an isozyme selective delta protein kinase C inhibitor, a JAK3 enzyme inhibitor, a JNK inhibitor, a kinase inhibitor, a.kinesin antagonist, a leukotriene inhibitor and antagonist, a MAP kinase inhibitor, a matrix metalloproteinase inhibitor, an MCP-CCR2 inhibitor, an mTOR inhibitor, an mTOR kinase inhibitor, a microtubule inhibitor, an MIF inhibitor, a neurokinin antagonist, an NF kappa B inhibitor, a nitric oxide agonist, an ornithine decarboxylase inhibitor, a p38 MAP kinase inhibitor, a palmitoyl-protein thioesterase inhibitor, a PDGF receptor kinase inhibitor, a peroxisome proliferator-activated receptor (PPAR) agonist, a phosphatase inhibitor, a phosphodiesterase inhibitor, a PKC inhibitor, a platelet activating factor antagonist, a prolyl hydroxylase inhibitor, a polymorphonuclear neutrophil inhibitor, protein kinase B inhibitor, protein kinase C stimulant, purine nucleoside analogue, a purineoreceptor P2X antagonist, a Raf kinase inhibitor, reversible inhibitor of ErbBi and ErbB2, ribonucleoside triphosphate reductase inhibitor, an SDF-1 antagonist, a sheddase inhibitor, an SRC inhibitor, a stromelysin inhibitor, an Syk kinase inhibitor, a telomerase inhibitor, a TGF beta inhibitor, a TNF-alpha antagonist or TACE inhibitor, a tumor necrosis factor antagonist, a Toll receptor inhibitor, a tubulin antagonist, a protein tyrosine kinase inhibitor, a VEGF inhibitor, a vitamin D receptor agonist, a retinoic acid receptor antagonist, a heat shock protein 90 antagonist, a steroid, a cell cycle inhibitor, a histone deacetylase inhibitor, an anti-microbial agent, an intracellular calcium flux inhibitor, an microtubule inhibitor, an HMGCoA reductase inhibitor, an actin polymerization and stabilization promoter, a tyrosine kinase inhibitor, a TGF beta inhibitor, a TNF-alpha antagonist, a TACE inhibitor, a calcineurin inhibitor, a peptidyl-prolyl cis/trans isomerase inhibitor, an apoptosis activator, an antimetabolite and antineoplastic agent, a TGF beta inhibitor, a DNA methylation promoter, and a PKC inhibitor ZD-6474, AP-23573, synthadotin, S-0885, aplidine, ixabepilone, IDN-5390, SB-2723005, ABT-518, combretastatin, anecortave acetate, SB-715992, temsirolimus, adalimumab, erucylphosphocholine, alphastatin, etanercept, humicade, gefitinib, isotretinoin, radicicol, clobetasol propionate, homoharringtonine, trichostatin A, brefeldin A, thapsigargin, dolastatin 15, cerivastatin, jasplakinolide, herbimycin A, pirfenidone, vinorelbine, 17-DMAG, tacrolimus, loteprednol etabonate, juglone, prednisolone, puromycin, 3-BAABE, cladribine, mannose-6-phosphate, 5- azacytidine, Ly333531 (ruboxistaurin), and simvastatin.

All patents, patent applications, publications, and descriptions mentioned above are herein incorporated by reference in their entirety for all purposes. None is admitted to be prior art.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents. And, as will be understood by those skilled in the art, the present invention may be embodied in other specific forms without departing from the essential characteristics thereof. These other embodiments are intended to be included within the scope of the present invention, which is set forth in the following claims.

What is claimed is:

1. A device for use in an eye with elevated intraocular pressure or glaucoma, the device comprising
   a tubular body portion comprising a plurality of lumens,
   wherein each lumen terminates at an inlet section at a first end of the tubular body and at an outlet section at a second end of the tubular body, and
   wherein one or more of the plurality of lumens are selectively controllable between an open position and closed position,
   wherein when any of said lumens are open, said device is configured to divert intraocular fluid from a vitreous cavity to a subconjunctival space;
   wherein the inlet section comprises a first flange-like structure or first securing structure in close apposition to an intraocular surface; and
   wherein the outlet section is in fluid communication with the inlet section and comprises a second flange-like structure or second securing structure that is configured to rest on the sclera.

2. The device of claim 1, wherein the tubular body portion has an 18 gauge or less external size.

3. The device of claim 1, wherein the tubular body portion is adapted and configured for placement in isolation at a pars plana to provide for direct intraocular fluid flow from the vitreous cavity to the subconjunctival space.

4. The device of claim 1, wherein the tubular body portion is adapted and configured for placement in direct or indirect connection with one or more devices in the subconjunctival space that are intended to enhance and/or direct intraocular fluid flow from the vitreous cavity to the subconjunctival space.

5. The device of claim 1, wherein the inlet section comprises a clogging minimizing structure that minimizes clogging of the fluid communication at the inlet section by formed vitreous, blood, intraocular tissues, or scar formation, wherein the clogging minimization structure comprises multiple ports in fluid communication with each of the lumens.

6. The device of claim 1, wherein at least one lumen comprises a flow regulating member.

7. The device of claim 6, wherein the flow regulating member is selected from the group consisting of a plurality of nanotubes, a plurality of capillary tubes, a plurality of collimated passages and combinations thereof.

8. The device of claim 6, wherein the flow regulating member comprises a biological mechanoprotein used to regulate fluid flow.

9. The device of claim 6, wherein the flow regulating member is a membrane or a micromechanical valve.

10. The device of claim 1, wherein said lumens are selectively openable in situ.

11. The device of claim 10, wherein each of the lumens is initially closed and irreversibly openable.

12. The device of claim 11, wherein at least one of the irreversibly openable lumens comprises a soluble barrier that is initially non-patent and over time due to the time-dependent erosion, dissolution or decomposition of the soluble barrier becomes patent.

13. The device of claim 11, wherein at least one of the irreversibly openable lumens comprises a barrier such as a membrane or plug that is initially non-patent and selectively opened using an external laser.

14. The device of claim 11, wherein at least one of the irreversibly openable lumens comprises a barrier such as a membrane or plug that is initially non-patent and selectively opened using an external mechanical probe.

15. The device of claim 10, wherein each of the lumens has a size that is different from the other lumen.

16. The device of claim 15, wherein the size is between about 20 and 50 gauge.

17. The device of claim 10, wherein each of the lumens is labeled so as to be differentiated from the other lumen.

18. The device of claim 17, wherein at least one lumen is labeled by color.

19. The device of claim 1, wherein the inlet section comprises an anti-clogging shaped structure selected from the group consisting of a spiral, a screw, or a helix-shaped structure and combinations thereof.

20. The device of claim 1, wherein the inlet section comprises a structure for minimizing clogging selected from the group consisting of a filter membrane, surface corrugations, a surrounded cage structure, surface ridges, multiple ports, multiple perforations, and combinations thereof.

21. The device of claim 1, wherein the outlet section comprises the second flange-like structure which is larger than the tubular body portion.

22. The device of claim 1, wherein the inlet section comprises the first flange-like structure which is larger than the tubular body portion.

23. The device of claim 1, wherein the tubular body portion comprises a securing structure and wherein the securing structure is selected from the group consisting of a tissue adhesive, one or more barbs, a threading mechanism, a structure for suture placement, and combinations thereof.

24. The device of claim 1, wherein the device is made of a biocompatible material selected from the group consisting of titanium, stainless steel, silicone, polyurethane, polylactic acid, polylactic alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, polyamide, parylene, and combinations thereof.

25. The device of claim 1, wherein the device has a drug-eluting coating.

26. The device of claim 25, wherein the drug-eluting coating comprises an anti-inflammatory agent.

27. The device of claim 26, wherein the anti-inflammatory agent is selected from the group consisting of corticosteroids, immunosuppressive agents, non-steroidal anti-inflammatory drugs, anti-inflammatory proteins, peptides, or nucleic acids, and combinations thereof.

28. The device of claim 25, wherein the drug-eluting coating comprises an anti-proliferative agent.

29. The device of claim 28, wherein the anti-proliferative is selected from the group consisting of a corticosteroid, an immunosuppressive agent, mitomycin, 5-fluorouracil, heparin, anti-proliferative proteins, peptides, or nucleic acids and combinations thereof.

30. The device of claim 25, wherein the drug-eluting coating comprises an anti-microbial agent.

31. The device of claim 25, wherein the drug-eluting coating comprises an intraocular pressure lowering agent.

32. The device of claim 25, wherein the drug-eluting coating comprises a vitreolytic agent.

33. The device of claim 32, wherein the vitreolytic agent is selected from the group consisting of a dispase, urea, collagenase, hyaluronidase, plasmin, microplasmin, chondroitinase, a protease, and combinations thereof.

34. A method for lowering intraocular pressure, comprising:
introducing into an eye a device comprising
a tubular body portion comprising a plurality of lumens,
wherein each lumen terminates at an inlet section at a first end of the tubular body and at an outlet section at a second end of the tubular body,
wherein one or more of the plurality of lumens are selectively controllable between an open position and closed position,
wherein when any of said lumens are open, said device is configured to divert intraocular fluid from a vitreous cavity to a subconjunctival space,
wherein the inlet section comprises a first flange-like structure or first securing structure in close apposition to an intraocular surface, and
wherein the outlet section is in fluid communication with the inlet section and comprises a second flange-like structure or second securing structure that is configured to rest on the sclera; and
diverting intraocular fluid from the vitreous cavity to the subconjunctival space at pars plana.

35. The method of claim 34, wherein the device is a self-contained transmural shunt device.

36. The method of claim 34, wherein the device resides entirely within the pars plana.

37. The method of claim 34, further comprising an eye surgery trabeculectomy.

* * * * *